(12) United States Patent
Strahan

(10) Patent No.: US 9,745,059 B2
(45) Date of Patent: Aug. 29, 2017

(54) SYSTEM TO ADAPT AN OPTICAL DEVICE TO CALCULATE A CONDITION VALUE

(71) Applicant: INFRARED CAMERAS, INC., Beaumont, TX (US)

(72) Inventor: Gary Eugene Strahan, Beaumont, TX (US)

(73) Assignee: INFRARED CAMERAS, INC., Beaumont, TX (US)

(*) Notice: Subject to any disclaimer, the term of this patent is extended or adjusted under 35 U.S.C. 154(b) by 855 days.

(21) Appl. No.: 14/194,562

(22) Filed: Feb. 28, 2014

(65) Prior Publication Data

US 2015/0268154 A1    Sep. 24, 2015

(51) Int. Cl.

| G01N 21/01 | (2006.01) |
| B64C 39/02 | (2006.01) |
| G01N 23/00 | (2006.01) |
| G01N 22/00 | (2006.01) |
| G01K 13/00 | (2006.01) |
| G01W 1/00 | (2006.01) |
| G01P 5/26 | (2006.01) |
| G01N 25/56 | (2006.01) |
| G01N 25/66 | (2006.01) |
| G01S 17/88 | (2006.01) |

(52) U.S. Cl.
CPC ............ *B64C 39/024* (2013.01); *G01K 13/00* (2013.01); *G01N 21/01* (2013.01); *G01N 22/00* (2013.01); *G01N 23/00* (2013.01); *G01N 25/56* (2013.01); *G01N 25/66* (2013.01); *G01P 5/26* (2013.01); *G01S 17/88* (2013.01); *G01W 1/00* (2013.01); *B64C 2201/127* (2013.01); *G01N 2021/015* (2013.01); *G01N 2021/0125* (2013.01); *G01N 2021/0137* (2013.01); *G01N 2021/0143* (2013.01)

(58) Field of Classification Search
CPC .......... G01N 21/00; G01N 2021/0118; G01N 2021/0125; G01N 2021/0131; G01N 2021/0137; G01N 2021/0143
See application file for complete search history.

(56) References Cited

U.S. PATENT DOCUMENTS

| 4,015,366 A * | 4/1977 | Hall, III ............... A01D 46/005 137/236.1 |
| 6,130,705 A | 10/2000 | Lareau et al. |
| 7,079,129 B2 | 7/2006 | Shigeta |
| 2007/0098397 A1 | 5/2007 | Chen et al. |
| 2008/0079843 A1 | 4/2008 | Pote et al. |
| 2009/0015674 A1 | 1/2009 | Alley et al. |

* cited by examiner

*Primary Examiner* — Huan Tran
(74) *Attorney, Agent, or Firm* — Rao DeBoer Osterrieder, PLLC; Dileep P. Rao

(57) ABSTRACT

A system usable to adapt an optical device to calculate a condition value. The system utilizes data from an optical device about a field of vision to calculate a condition value such as temperature for a target within the field of vision. The system makes use of an adapter connected to the optical device for transmitting adapter output data and a converter that accesses the adapter output data to calculate the condition value. The adapter components can weigh less than 3 ounces, and encompass a volume of less than 4 cubic inches, making it suitable for deployment on a drone, or remotely operated vehicle.

20 Claims, 4 Drawing Sheets

SYSTEM TO ADAPT AN OPTICAL DEVICE TO CALCULATE A CONDITION VALUE

FIELD

The present embodiments generally relate to a system to adapt an optical device for calculating a condition value such as temperature for objects in the visual field of the optical device.

BACKGROUND

A need exists for a system capable of receiving data from an optical device and converting the data to a condition value.

Current optical devices, such as infrared cameras and visible spectrum cameras have various physical structures and data output mechanisms. A need exists for a system that can easily be adapted to interface with multiple types of optical devices.

A further need exists for a system to access the native data of optical devices and calculate pertinent information about conditions in the visual field of the optical device.

Numerous applications spanning multiple industries exist for such a system. For example, temperature distribution analysis of industrial equipment can be conducted to identify potential failures or weak points. Condition values of crops can be analyzed to identify insect intrusion, or diseased plants, plant under or overwatering, and potential crop yield.

Condition values, such as temperatures, can provide invaluable information for analysis in applications spanning multiple industries. A need exists for a lightweight and miniature system capable of being installed on a drone, or unmanned flight vehicle for remote use capable of collecting and supplying condition values. Remote use of such a system allows for rapid data collection, data collection in difficult to reach areas, and data from otherwise impractical perspective views.

The present embodiments meet these needs.

BRIEF DESCRIPTION OF THE DRAWINGS

The detailed description will be better understood in conjunction with the accompanying drawings as follows.

Figure 1:
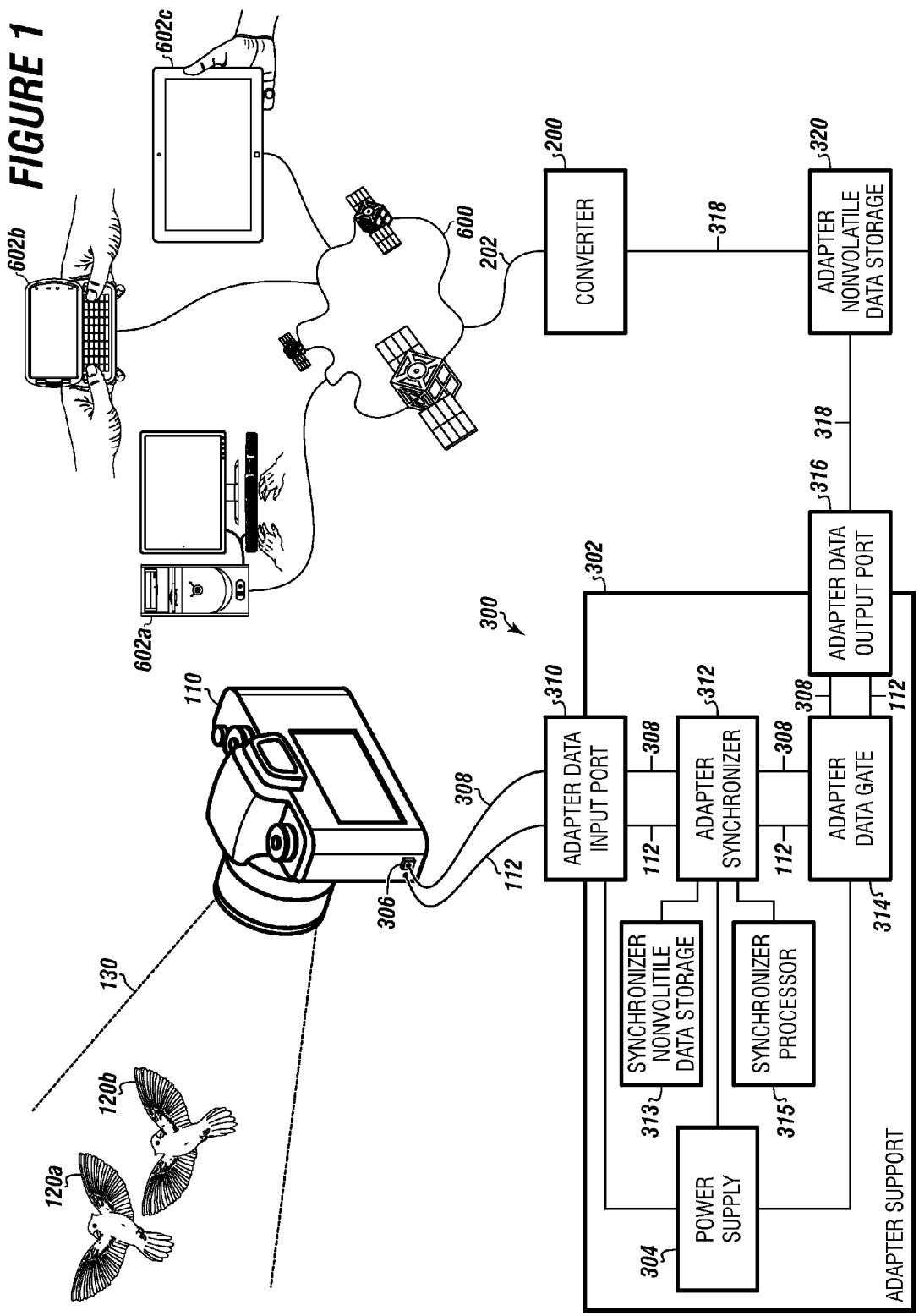
FIG. 1 is a schematic diagram of a system for adapting an optical device to calculate a condition value.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

Specific structural and functional details disclosed herein are not to be interpreted as limiting, but merely as a basis of the claims and as a representative basis for teaching persons having ordinary skill in the art to variously employ the present invention.

The term "optical device" as used herein refers to a device that detects, manipulates, or measures electromagnetic radiation in a field of vision. The optical device can be capable of outputting data regarding electromagnetic radiation in a field of vision.

The term "field of vision" as used herein refers to an area or volume within which an optical device can detect electromagnetic radiation.

The term "electromagnetic radiation" as used herein refers to radiant energy possessing both a frequency and a wavelength. Examples of electromagnetic radiation include, but are not limited to radio waves, microwaves, infrared radiation, visible light, ultraviolet radiation, x-rays, and gamma rays.

The term "resistive type device (RTD)" or "pixel" as used herein refers to a single component that measures radiant energy carried by electromagnetic radiation and converts the measurement to an electrical signal.

The term "adapter" as used herein refers to a set of components for use with the system of the present invention. The adapter can be an integrated piece, or a collection of individual components. The adapter is intended to refer to a collection of devices that perform the function intended by the present invention.

The term "sensor" as used herein refers to a device that measures one or more variables and converts the measurement to an electrical signal.

The terms "port", "input port", and "output port" as used herein refer to connections for the transfer of analog or digital data. The port can refer to a wireless connection, or a physical connection.

The term "bolometer" as used herein refers to a device for measuring the power of incident electromagnetic radiation.

The term "microbolometer" as used herein refers to a specific type of bolometer that measures electromagnetic radiation in the infrared spectrum.

The term "focal plane array" as used herein refers to a group of RTDs or pixels.

The term "camera" as used herein refers to an optical device that can detect and record electromagnetic radiation in a field of vision. The detected information can be stored, transmitted to another location, or both. A camera can be designed specifically for a specific type of electromagnetic radiation such as infrared radiation, or visible light radiation.

The term "target" as used herein refers to an object or a region within the field of vision of an optical device. The target can be any desired object or region that a user of the present invention wishes to identify a condition value for.

The term "target background" as used herein refers to an object or a region within the field of vision of an optical device that is not the desired object or region that a user of the present invention wishes to identify a condition value for.

The term "condition value" as used herein refers to information about a target that can be extrapolated and calculated using data from an optical instrument and by using other known information. Some examples of condition values include temperature, heat distribution, radioactivity, and any other characteristics of a target that can be calculated using data from an optical instrument.

The term "drone" as used herein refers to an unmanned vehicle that can be operated by remote control. Drone can refer to vehicles with or without flight capability. Drone can also refer to vehicles deployed on or under water.

The term "MIPI Alliance" as used herein refers to a global, collaborative organization comprised of companies that span the mobile ecosystem and are committed to defining and promoting interface specifications for mobile devices. At the time of this writing, the MIPI Alliance maintains a website viewable at www.MIPI.org.

Many optical devices can perceive, record, and transmit data about electromagnetic radiation that is emitted or reflected from an object in their field of vision. The radiation from an object in a field of vision can be translated into data by the optical device. A widely used method for translating detected electromagnetic radiation into data is to use resistive type devices (RTDs), often referred to as pixels.

Many optical devices make use of a bolometer, a device for measuring the power of incident electromagnetic radiation that can include an array of measuring elements. Devices such as infrared cameras can use microbolometers, which are a specific type of bolometer that measure electromagnetic radiation in the infrared spectrum.

As cameras are widely understood examples of optical devices, the embodiments and descriptions below regarding an optical device many times make specific reference to a camera. However, the structural and functional details disclosed herein as well as their usage can be translated to any other optical devices with a field of vision and the capability to transmit or record data, whether or not specifically discussed herein.

In optical devices such as visible light cameras, a focal plane array (FPA) designed for detecting visible light comprising an RTD array can be used. In other cameras, a microbolometer comprising an RTD array for detecting infrared light can be used. The detection mechanism most commonly used is an array of RTDs designed for the specific application. Data from RTDs are referenced in examples, but data from other electromagnetic radiation detection means can be substituted for use with the present invention.

As emitted or reflected radiation from an object is focused on a camera's RTD array (i.e. an FPA or a microbolometer), an electrical signal can be generated by each individual RTD. This electrical signal can be converted to data by the camera. This data can be stored or transmitted by the camera as an optical device data.

By monitoring some additional environmental conditions, the optical device data can be converted to a condition value by the present invention. The present invention is unique in that it can work in conjunction with any optical device with a data output.

Further, the lightweight and miniature design of the present invention allow for it to be used in applications where allowable space and allowable weight are limited. For example, the system can be fully disposed on a portable camera which is easily carried by a user, or deployed on an unmanned land vehicle, deployed on an unmanned vehicle for use on or under water, or deployed on an unmanned flight vehicle with limited available footprint for accessories and limited weight bearing capability.

The present embodiments refer to a system for adapting an optical instrument to measure a condition value such as temperature. The system can comprise an adapter capable of attaching to an optical device to receive optical device data and communicating the optical device data to a converter. The communication can be direct, such as by wireless transmission of optical device data to the converter, or indirect, such as by storing optical device data for later access by the converter.

The adapter can be designed to be miniature and lightweight. The adapter can comprise a power supply, and in some embodiments supply power to the optical device or other connected devices. Alternatively, the adapter can be in communication with a remote or external power supply.

The adapter can further comprise one or more adapter sensors for monitoring ambient conditions in order to accurately calculate a condition value. The adapter sensors can monitor various ambient conditions such as temperature, air pressure, relative humidity, dew point, precipitation, wind speed and direction, cloud cover, or other ambient variables.

For example, adapter sensors connected to the adapter support or in communication with the adapter can monitor and generate adapter sensor data from conditions such as ambient air temperature, humidity, precipitation, temperature within the optical device being used, temperature of a lens of the optical device being used, temperature of the case or housing of the optical device being used, temperature of a shutter of the optical device being used, and other similar variables.

The adapter can comprise an adapter data input port for receiving the optical device data. The adapter data input port can be in the form of a wireless receiver for receiving data from optical devices able to transmit wireless data, or a physical port for connection to the optical device. Optical device data can comprise analog or digital data.

The adapter data input port can be a physical port commonly used for data communication such as a camera serial interface port or a camera parallel interface port (such as various ports specified by the MIPI Alliance), an Ethernet port, a port complying with IEEE 1394 standards (commonly called a FireWire port), a port complying with IEEE 1284 standards, a PS/2 port, a port complying with RS-232 standards, a Universal Serial Bus (USB) port, a Video Graphics Array (VGA) port, a Digital Visual Interface (DVI) port, a Small Computer System Interface (SCSI) port, a High-Definition Multimedia Interface (HDMI) port, a tip/ring/sleeve (TRS) port, and the like.

The adapter data input port can be a parallel port or a serial port, allowing the adapter to receive data from a multitude of optical devices in a multitude of data formats. The optical device data can include data related to objects in the visual field of the optical device such as data from an RTD array, data from any sensors located upon the optical device such as a temperature sensor, an altimeter, or any other data capable of being outputted by the optical device. The adapter data input port can be specifically designed to communicate with an optical device output, or make use of other adapters to communicate with the optical device and receive optical device data.

The adapter can optionally comprise an adapter synchronizer for synchronizing the adapter sensor data with the optical device data. The adapter synchronizer ensures that different pieces of data being used are not time shifted with respect to each other.

The adapter synchronizer can be a physical mechanism, such as a mechanism that delays various types or pieces of data for preset amounts of time in order to synchronize the data, one or more resistors selectively placed in series with incoming adapter sensor data, optical device data, or combinations thereof. The adapter synchronizer can alternatively be a software mechanism, such as computer instructions instructing a processor to perform a correlation of clock values with data, a correlation of time stamps with data, or similar methods.

The adapter can further comprise an adapter data output port for transmitting adapter output data. The adapter data output port can be a wireless port, or a physical port used for data communication as discussed above.

The adapter data output port can transmit any received data as an adapter output data to a nonvolatile data storage or to a converter. The received data can comprise items such as the adapter sensor data, and the optical device data.

The adapter can further comprise an adapter data gate for either throughputting any received data as an adapter output data, or combining the received data as an adapter output data. For example, in embodiments where an adapter synchronizer is not used, the adapter data gate can simply throughput adapter sensor data and optical device data to a converter for synchronization to occur at the converter. In other embodiments, the adapter data gate can combine and transform data to a desired output format. For example, the adapter data gate can translate analog data into digital data for use by the converter, or translate data received from a parallel port for use by a serial port.

The adapter can incorporate a printed circuit board (PCB) which connects or incorporates some or all of the adapter elements discussed above. For example, the adapter sensors, the adapter data input port, and the adapter data output port can all be part of a PCB or connected to a PCB. The PCB can act as the adapter support.

The converter can receive the adapter output data and convert the adapter output data to a condition value of a target within the field of vision of the optical device. The converter can be a hardware device, such as a PCB with instructions for accomplishing the temperature conversion hard wired in. Or, for greater flexibility, the converter can be implemented using software and a computer.

The converter, when implemented using software, can comprise a computer with a computer data input port, a computer nonvolatile data storage, a computer processor, and a computer data output port. The nonvolatile data storage can comprise a conversion module having computer instructions to convert the adapter output data into a condition value.

The computer nonvolatile data storage can further comprise a calibration module having computer instructions to calibrate the temperature value based upon data from the adapter sensors and based upon data from the optical device. For the most accurate condition readings, each optical device can be calibrated with the adapter prior to using the optical device in conjunction with the adapter.

For example, the adapter can be connected to an optical device in a controlled environment. The controlled environment can be controlled for various characteristics, such as ambient light, ambient temperature, temperature distribution, target distance, target condition value, and the like.

The optical device can then be used to acquire data from various control subjects at known condition values. The calibration module can receive data from the adapter, including data from the optical device, data from adapter sensors, and data from an adapter synchronizer.

The calibration module can then generate a calibration data for use by the conversion module in adjusting the condition value. The calibration data can include other characteristics of the optical device that include, but are not limited to information regarding non-functional RTDs, information regarding inaccurate RTDs, or performance variations of the optical device within the field of vision of the optical device.

The calibration module can further correlate optical device data and adapter sensor data with the known condition values of the control subjects.

Using all the data from the calibration module, a conversion algorithm can be generated for converting optical device data to a condition value. Based upon the application, persons having ordinary skill in the art can conduct various calibration steps in controlled conditions, utilizing a variety of adapter sensors and a variety of optical devices.

For example, if the requisite condition value of a target is temperature, a plurality of targets at various known temperatures can be present in a controlled environment. The background temperatures can also be known. The various known temperatures can encompass the range of temperatures desired to be measured by a user.

Adapter sensors such as a case surface temperature sensor, a lens temperature sensor, a shutter temperature sensor, a detector temperature sensor, an RTD temperature sensor, an ambient air temperature sensor, an air pressure sensor, a relative humidity sensor, a dew point sensor, a precipitation sensor, a wind speed sensor, a wind direction sensor, a cloud cover sensor, and the like can be used.

An optical device, such as a camera, can be used to output optical device data from its field of vision to a converter. The field of vision can encompass the targets and backgrounds in the controlled environment.

The converter can then fit an algorithm that describes the relationship between the adapter sensor data and the optical device data to the known temperatures of the targets and the known temperatures of the background in the controlled environment.

The algorithm can be specific to the optical device for the greatest accuracy of condition values, in this instance, temperatures. It is feasible to base the algorithm on a similar optical device if a greater error range in calculated condition values is acceptable.

Once an optical device has been calibrated with the converter, the converter can calculate condition values of targets with unknown condition values based upon the generated algorithm and adapter output data received from targets in other fields of vision of the optical device.

The adapter can be constructed in a manner such that it weighs less than 3 ounces and have a volume of less than 4 cubic inches. This allows for a great deal of flexibility in implementing the present invention in various applications. Current methods and apparatuses are too bulky for many applications allowed by the present invention.

For example, the adapter can be light enough, and miniature enough to be used on a remotely controlled drone with flight capability. The drone can carry an optical device connected to the adapter and either store the adapter output data, or wirelessly transmit the adapter output data to a converter.

Turning now to the Figures, FIG. 1 is a schematic diagram of a system for adapting an optical device to calculate a condition value.

In this embodiment, the system can have an optical device 110, wherein the optical device 110 transmits or stores optical device data 112 about a field of vision 130. The optical device 110 can be any device capable of detecting or recording electromagnetic radiation.

Some examples of optical devices 110 usable with the system can include a visible spectrum detector or camera, an infrared detector or camera, an ultraviolet radiation detector or camera, a terahertz camera, a ground penetrating radar device, an x-ray detector or camera, a gamma ray detector or camera, a cosmic ray detector or camera, a microwave detector or camera, a radio wave detector or camera, a lidar detector or camera, and a laser imaging detector or camera.

The field of vision 130 can be the area or volume for which the optical device 110 is detecting or recording electromagnetic radiation. For example, a visible spectrum camera can have a field of vision 130 that encompasses all areas and volumes visible through its lens.

One or more targets 120*a* and 120*b* can be within the field of vision. The targets can be any object or area that the optical device 110 can detect or record electromagnetically. The targets 120*a* and 120*b* are shown as birds.

The optical device data 112 can be in an analog or digital format, and can comprise information about electromagnetic radiation detected within a field of vision 130. The optical device data 112 can also comprise information from sensors or other components of the optical device 110 capable of transmitting data.

This embodiment shows an adapter 300 in communication with the optical device 110 for receiving the optical device data 112. The adapter can have an adapter support 302. The adapter support can be a flat plate, a circuit board, a housing, or any other structure that allows various adapter components to be supported and in communication with each other.

The adapter 300 can have an adapter power supply 304 connected to the adapter support 302. In alternate embodiments, adapter power can come from an external power supply in communication with the adapter 300.

The adapter 300 can have at least one adapter sensor 306 in communication with the adapter. The embodiment shown has a case surface sensor disposed on the body of the optical device 110. The adapter sensor 306 can be used to collect information about the ambient conditions that the optical device 110 is operating in. This information can be used for calculating a condition value 202 as discussed below.

In embodiments, various other sensors can be used as needed for specific applications. For example, other sensors can be a case surface temperature sensor, a lens temperature sensor, a shutter temperature sensor, a detector temperature sensor, an RTD temperature sensor, an ambient air temperature sensor, an air pressure sensor, a relative humidity sensor, a dew point sensor, a precipitation sensor, a wind speed sensor, a wind direction sensor, a cloud cover sensor, and the like.

The adapter 300 can have at least one adapter data input port 310 connected to the adapter support 302 for receiving the optical device data 112 and receiving the adapter sensor data 308. While the present embodiment shows a single port, multiple input ports can be used for multiple sensors.

The adapter data input port 310 can be various ports in use by optical devices. Based upon the type of data transmitted by the optical device 110, the data input port 310 can be a parallel port or a serial port. As to form factor, the adapter data input port 310 can be any form used by an optical device.

In embodiments, various ports can be used such as: a wireless port, a camera serial interface port, a camera parallel interface port, an Ethernet port, a port complying with IEEE 1394 standards, a port complying with IEEE 1284 standards, a PS/2 port, a port complying with RS-232 standards, a universal serial bus (USB) port, a video graphics array (VGA) port, a digital visual interface (DVI) port, a small computer system interface (SCSI) port, a high-definition multimedia interface (HDMI) port, a tip/ring/sleeve (TRS) port, and the like.

In embodiments, the adapter 300 can comprise an adapter synchronizer 312 connected to the adapter support 302 for synchronizing the adapter sensor data 308 with the optical device data 112. The adapter synchronizer 312 can ensure that data received from the optical device 110 and the adapter sensor 306 are not time shifted with respect to each other.

The adapter synchronizer 312 can be any means of time synchronizing data, for example: a circuit board with a hardwired instruction, an electronic component for selectively delaying certain data, computer instructions in a synchronizer nonvolatile data storage 313 instructing a synchronizer processor 315 to correlate the adapter sensor data 308 with the optical device data 112 using a time identifier of the adapter sensor data 308 and a time identifier of the optical device data 112, or other similar mechanisms.

The adapter 300 can have an adapter data gate 314 in communication with the adapter data input port 310. The adapter data gate 314 can combine the optical device data 112 and the adapter sensor data 308, or simply throughput the optical device data 112 and the adapter sensor data 308.

The adapter data gate 314 is shown simply throughputting the optical device data 112 and the adapter sensor data 308.

The adapter 300 can have at least one adapter data output port 316 connected to the adapter support 302 for transmitting an adapter output data 318 to an adapter nonvolatile data storage 320 or to a converter 200. The adapter output data can comprise the adapter sensor data 308 and the optical device data 112.

The adapter data output port 316 can be of any desired form factor. Various ports, as discussed for the adapter data input port 310 can be used as desired.

The adapter output data is shown in this embodiment being output to an adapter nonvolatile data storage 320. In other embodiments, the adapter output data can be directly transmitted to the converter 200.

The system can have a converter 200, wherein the converter calculates a condition value 202 and outputs the condition value 202. The converter can simultaneously output the condition value 202 to a plurality of locations 602*a*-602*c*, such as a display, a client device, a printer, a nonvolatile data storage, an application programming interface, and the like. Examples shown in this Figure include an application programming interface 602*a* for a program residing on a computer, a client device such as a cellular phone 602*b*, and a client device such as a tablet computer 602*c*.

The converter can output the condition value 202 directly to a location, or via a network 600.

In the embodiment shown, the converter accesses the adapter output data 318 from the adapter nonvolatile data storage 320. In alternative embodiments, the converter can directly receive the adapter output data 318 from the adapter 300, for example using a wireless connection.

In alternative embodiments, the adapter nonvolatile data storage 320 can also be connected to the adapter support 302.

Figure 2:
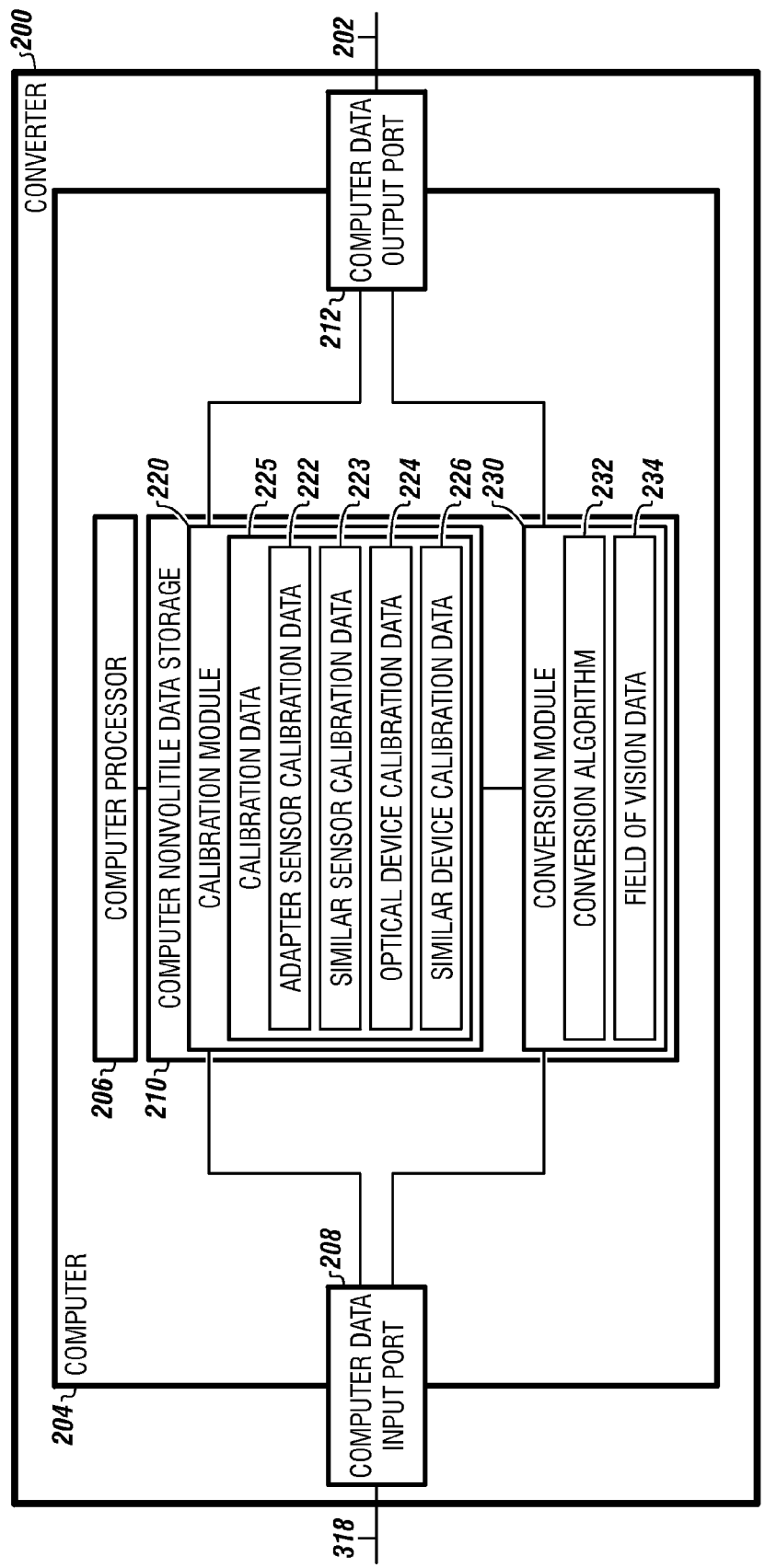
FIG. 2 shows a schematic of a converter according to one or more embodiments.

FIG. 2 shows a schematic of a converter according to one or more embodiments.

In embodiments, the converter 200 can comprise a computer 204. The computer can have a computer processor 206, a computer data input port 208 for receiving the adapter output data 318, a computer nonvolatile data storage 210 in communication with the computer processor 206 and the computer data input port 208.

The computer nonvolatile data storage 210 can have a calibration module 220 and a conversion module 230.

The calibration module 220 can have calibration data 225, including an adapter sensor calibration data 222, a similar sensor calibration data 223, an optical device calibration data 224, a similar device calibration data 226, and combinations thereof.

The adapter sensor calibration data 222, the similar sensor calibration data 223, the optical device calibration data 224, and the similar device calibration data 226 can be acquired in a controlled environment with known condition values and a controlled ambient condition.

The calibration data 225 can be used to adjust for ambient condition information provided by the adapter sensor data, as well as characteristics of a specific optical device.

For example, if the desired condition value to be calculated is a temperature, one method of generating the calibration data 225 is by using known condition values in a controlled environment as described below.

A controlled environment, such as a laboratory type setting, can be selected in which ambient conditions are carefully controlled. The ambient conditions to be controlled can vary based on the desired condition value 202. In this example, ambient conditions pertinent to the condition value to be calculated (temperature) such as ambient temperature and ambient thermal distribution are carefully maintained at a desired level.

One or more controlled targets at different known condition values (temperatures) can be introduced into the controlled environment. The optical device, which can be an infrared camera in this instance, can transmit optical device data about the controlled environment to the adapter.

The adapter can receive the optical device data, and also receive adapter sensor data about the controlled environment. Adapter sensors to be utilized can be chosen for the desired condition value to be calculated and the desired ambient conditions to be monitored.

In this example, sensors such as a case surface temperature sensor (for the case of the optical device), a lens temperature sensor, a shutter temperature sensor, a detector temperature sensor, an RTD temperature sensor, an ambient air temperature sensor, or any combination thereof can be utilized.

The adapter can then transmit adapter output data to the calibration module 220 to generate the calibration data 225, including adapter sensor calibration data 222 and optical device calibration data 224. Optionally, the calibration data 225 can comprise similar sensor calibration data 223 or similar device calibration data 226, such as from a similar adapter sensor or a similar optical device that had been previously calibrated in this manner.

Ambient conditions can be selectively varied to generate additional calibration data. The calibration data can then be used to fit a mathematical function describing the relationship between the condition value (temperature) and adapter output data (which is comprised of the optical device data and the adapter sensor data).

In embodiments, the conversion module can have a conversion algorithm 232 incorporating the mathematical function described above used for calculating the condition value 202 using a field of vision data 234 and the calibration data 225. The field of vision data can be the adapter output data 318, or other data originating from the optical device, such as a data stored in the adapter nonvolatile data storage, a manually inputted data, a historical data for the optical device, and the like.

For embodiments in which an adapter synchronizer is not used, the conversion module 230 can time synchronize the adapter output data 318.

In embodiments, the conversion algorithm 232 can be based on the calibration data 225, to correct the condition value 202 for ambient conditions.

In embodiments, the conversion module can allow a user to select a target from the field of vision data 234. The condition value 202 can be calculated for this target. The converter can then output the condition value 202, such as by using a computer data output port 212.

Figure 3:
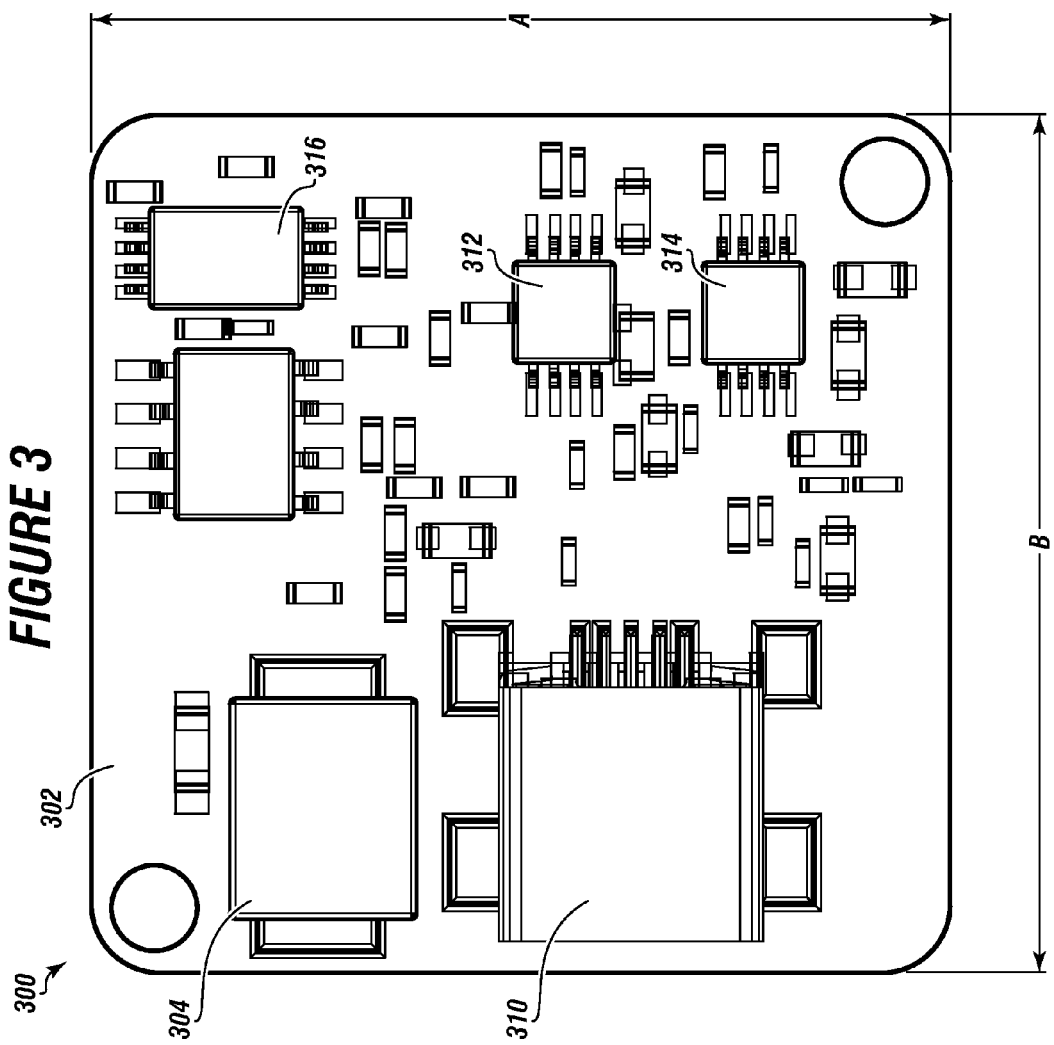
FIG. 3 shows an adapter according to one or more embodiments.

FIG. 3 shows the adapter according to one or more embodiments.

In this embodiment, the adapter 300 can have an adapter support 302 which is shown as a printed circuit board with surface mounted components. The elements shown in FIG. 1 as a schematic can be incorporated as components of the circuit board.

The adapter data input port 310 can communicate with the other components through printed electronic communication pathways on the circuit board. The adapter 300 can have an adapter power supply 304, an adapter synchronizer 312, and an adapter data gate 314.

In this embodiment, the adapter data output port 316 can be a different type of port than the adapter data input port 310. For example the adapter data input port 310 can be a camera serial interface port and the adapter data output port 316 can be a USB port.

As shown in this embodiment, the adapter synchronizer 312 and the adapter data gate 314 can be surface mounted on the circuit board. In other embodiments, the adapter synchronizer 312 and the adapter data gate 314 can be incorporated into the design of the circuit board.

In this embodiment, the adapter support 302 can have width and length which are equal to or less than 2 inches, and a depth of less than 1 inch. The adapter can weigh less than 3 ounces, making it suitable for mounting on various optical devices without undue encumbrance.

Figure 4:
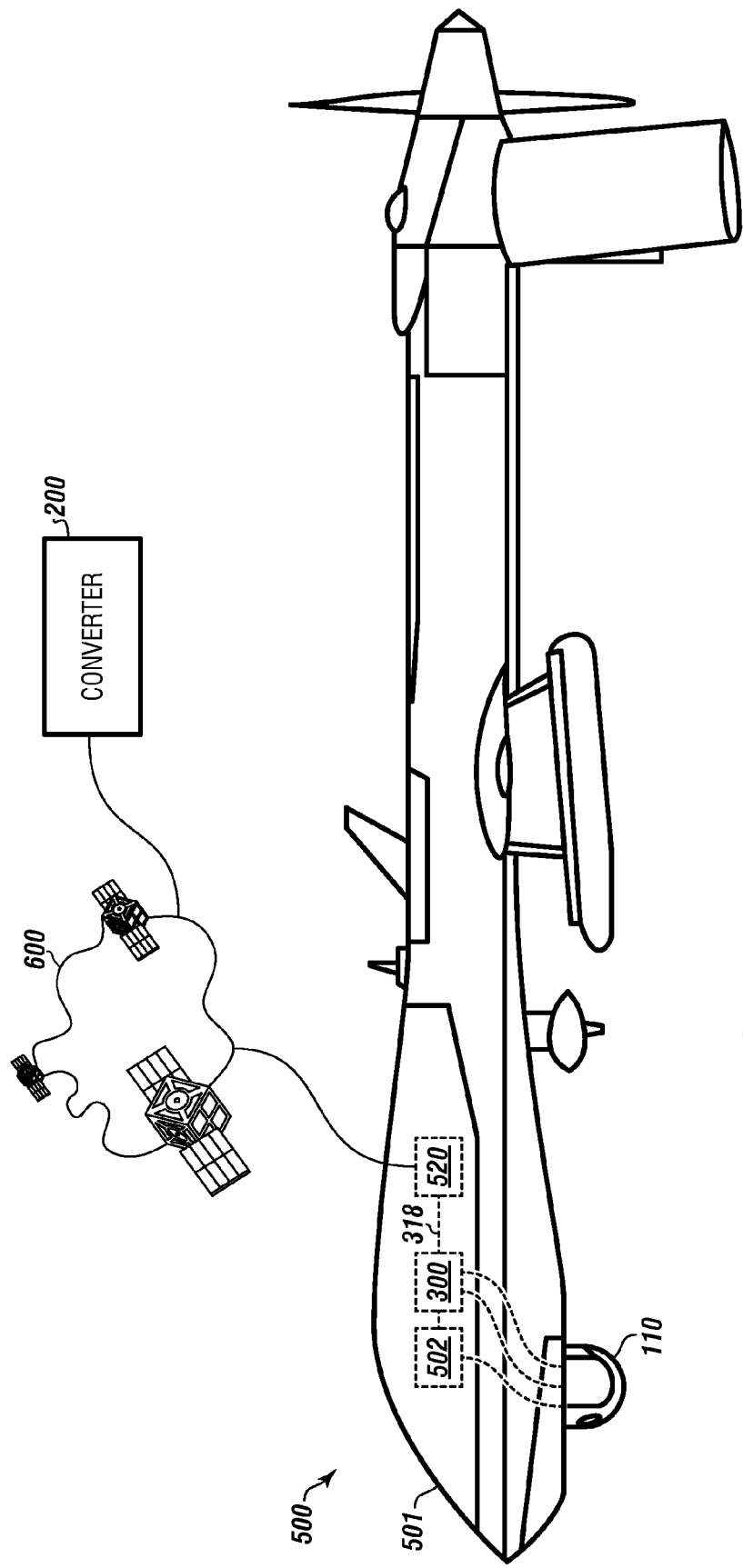
FIG. 4 shows a drone with the system for adapting an optical device to calculate a condition value.

FIG. 4 shows a drone with the system for adapting an optical device to calculate a condition value.

In this embodiment, a drone 500 with the system for adapting an optical device to calculate a condition value is shown. The drone can have a drone body 501 with an optical device 110 mounted thereon. The drone body can further support a drone power supply 502, an adapter 300 providing adapter output data 318, and a drone wireless connection 520 in communication with the converter 200 via a network 600.

The drone can be remotely controlled and deployed in various applications wherein a user of the present invention wishes to collect condition values. For example, a drone can be flown over farmland to collect condition values of crops, which can be analyzed to identify insect intrusion, diseased plants, and the like.

A flying drone with the system for adapting an optical device to calculate a condition value is shown. In alternate embodiments, the drone can be a land vehicle, a water surface vehicle, an underwater vehicle, and the like.

In alternate embodiments, a drone data storage can be substituted for the drone wireless connection 520 for later access by the converter 200.

The embodiment shown in FIG. 3 is an example of an adapter 300 that is well suited for employing in conjunction with a drone, due to its light weight and small volume.

While these embodiments have been described with emphasis on the embodiments, it should be understood that within the scope of the appended claims, the embodiments might be practiced other than as specifically described herein.

What is claimed is:

1. A system for adapting an optical device to calculate a condition value for a target within a field of vision, wherein the system comprises:
   a. the optical device, wherein the optical device transmits or stores optical device data about the field of vision;
   b. an adapter in communication with the optical device for receiving the optical device data, comprising:
      (i) an adapter support;

(ii) an adapter power supply connected to the adapter support or an external power supply in communication with the adapter;
(iii) at least one adapter sensor in communication with the adapter;
(iv) at least one adapter data input port connected to the adapter support for receiving the optical device data and receiving adapter sensor data;
(v) an adapter data gate in communication with the adapter data input port for at least one of: combining the optical device data and the adapter sensor data, or throughputting the optical device data and the adapter sensor data;
(vi) at least one adapter data output port connected to the adapter support for transmitting adapter output data to an adapter nonvolatile data storage or to a converter, wherein the adapter output data comprises:
 1. the adapter sensor data; and
 2. the optical device data; and
c. the converter, wherein the converter:
 (i) calculates a condition value by at least one of:
  1. accessing the adapter output data from the adapter nonvolatile data storage; and
  2. directly receiving the adapter output data; and
 (ii) outputs the condition value.

2. The system of claim 1, wherein the converter outputs the condition value directly or via a network to a plurality of client devices.

3. The system of claim 1, wherein the adapter further comprises an adapter synchronizer connected to the adapter support for synchronizing the adapter sensor data with the optical device data, wherein the adapter synchronizer is at least one of:
a. a circuit board with a hardwired instruction for time synchronizing the optical device data and the adapter sensor data;
b. an electronic component for selectively delaying the optical device data or the adapter sensor data; and
c. computer instructions in a synchronizer nonvolatile data storage instructing a synchronizer processor to correlate the adapter sensor data with the optical device data using a time identifier of the adapter sensor data and a time identifier of the optical device data.

4. The system of claim 1, wherein the optical device is at least one of:
a. a visible spectrum detector or camera;
b. an infrared detector or camera;
c. an ultraviolet radiation detector or camera;
d. a terahertz camera;
e. a ground penetrating radar device;
f. an x-ray detector or camera;
g. a gamma ray detector or camera;
h. a cosmic ray detector or camera;
i. a microwave detector or camera;
j. a radio wave detector or camera;
k. a lidar detector or camera; and
l. a laser imaging detector or camera.

5. The system of claim 1, wherein the adapter sensor comprises at least one of:
a. a case surface temperature sensor;
b. a lens temperature sensor;
c. a shutter temperature sensor;
d. a detector temperature sensor;
e. a resistive type device temperature sensor;
f. an ambient air temperature sensor;
g. an air pressure sensor;
h. a relative humidity sensor;
i. a dew point sensor;
j. a precipitation sensor;
k. a wind speed sensor;
l. a wind direction sensor; and
m. a cloud cover sensor.

6. The system of claim 1, wherein the adapter data input port and the adapter data output port are each a serial data port or a parallel data port.

7. The system of claim 6, wherein the adapter data input port and the adapter data output port are each at least one of:
a. a wireless port;
b. a camera serial interface port;
c. a camera parallel interface port;
d. an Ethernet port;
e. a port complying with IEEE 1394 standards;
f. a port complying with IEEE 1284 standards;
g. a PS/2 port;
h. a port complying with RS-232 standards;
i. a universal serial bus (USB) port;
j. a video graphics array (VGA) port;
k. a digital visual interface (DVI) port;
l. a small computer system interface (SCSI) port;
m. a high-definition multimedia interface (HDMI) port; and
n. a tip/ring/sleeve (TRS) port.

8. The system of claim 1, wherein the converter comprises a computer, wherein the computer further comprises:
a. a computer processor;
b. a computer data input port for receiving the adapter output data;
c. a computer nonvolatile data storage in communication with the computer processor and the computer data input port, wherein the computer nonvolatile data storage comprises a conversion module to use the adapter output data to calculate the condition value; and
d. a computer data output port.

9. The system of claim 8, wherein the converter further comprises a calibration module comprising calibration data, wherein the calibration data comprises:
a. adapter sensor calibration data, or similar sensor calibration data; and
b. optical device calibration data or similar device calibration data; and
wherein the adapter sensor calibration data, the similar sensor calibration data, the optical device calibration data, and the similar device calibration data are acquired from the optical device in a controlled environment.

10. The system of claim 9, wherein the controlled environment comprises:
a. a controlled ambient condition; and
b. a controlled environment field of vision comprising:
 (i) at least one controlled target; and
 (ii) at least one known controlled target condition value.

11. The system of claim 9, wherein the conversion module comprises:
a. a conversion algorithm used for calculating the condition value, wherein the condition value has a mathematical relationship to the adapter output data;
b. computer instructions instructing the computer processor to receive a field of vision data, wherein the field of vision data comprises at least one of:
 (i) the adapter output data;
 (ii) data stored in the adapter nonvolatile data storage;
 (iii) manually inputted data; and (iv) historical data for the optical device;
c. computer instructions instructing the computer processor to time synchronize the adapter output data if necessary;
d. computer instructions instructing the computer processor to allow a user to select a target for which the condition value is calculated, wherein the target is selected from the field of vision data;
e. computer instructions instructing the computer processor to compare the field of vision data with the conversion algorithm to calculate the condition value;
f. computer instructions instructing the computer processor to adjust the condition value based upon the calibration data; and
g. computer instructions instructing the computer processor to output the condition value.

12. The system of claim 1, wherein the adapter support is a circuit board.

13. The system of claim 1, wherein the adapter support, the adapter power supply, the adapter data input port, the adapter data gate, and the adapter data output port have a combined weight of less than or equal to 3 ounces.

14. The system of claim 1, wherein the adapter support, the adapter power supply, the adapter data input port, the adapter data gate, and the adapter data output port have a combined volume of less than or equal to 4 cubic inches.

15. A drone, wherein the drone is an unmanned vehicle comprising:
a. a drone body for supporting a drone power supply, an optical device, and an adapter;
b. the drone power supply;
c. the optical device; and
d. the adapter, wherein the adapter comprises:
  (i) an adapter support;
  (ii) an adapter power supply connected to the adapter support or an external power supply in communication with the adapter;
  (iii) at least one adapter sensor in communication with the adapter;
  (iv) at least one adapter data input port connected to the adapter support for receiving optical device data and receiving adapter sensor data;
  (v) an adapter data gate in communication with the adapter data input port for at least one of: combining the optical device data and the adapter sensor data, or throughputting the optical device data and the adapter sensor data; and
  (vi) at least one adapter data output port connected to the adapter support for transmitting an adapter output data to an adapter nonvolatile data storage, to a drone data storage, to a drone wireless connection, or to a converter, wherein the adapter output data comprises:
    1. the adapter sensor data; and
    2. the optical device data.

16. The drone of claim 15, wherein the converter:
a. calculates a condition value by at least one of:
  (i) accessing the adapter output data from the drone data storage or the adapter nonvolatile data storage; and
  (ii) directly receiving the adapter output data; and
b. outputs the condition value.

17. The drone of claim 16, wherein the converter comprises a computer, wherein the computer further comprises:
a. a computer processor;
b. a computer data input port for receiving the adapter output data;
c. a computer nonvolatile data storage in communication with the computer processor and the computer data input port, wherein the computer nonvolatile data storage comprises a conversion module to use the adapter output data to calculate the condition value; and
d. a computer data output port.

18. The drone of claim 17, wherein the calibration data comprises:
a. adapter sensor calibration data, or similar sensor calibration data; and
b. optical device calibration data or similar device calibration data; and
wherein the adapter sensor calibration data, the similar sensor calibration data, the optical device calibration data, and the similar device calibration data are acquired in a controlled environment with known condition values.

19. The drone of claim 18, wherein the controlled environment comprises:
a. a controlled ambient condition; and
b. a controlled environment field of vision comprising:
  (i) at least one controlled target; and
  (ii) at least one known controlled target condition value.

20. The drone of claim 19, wherein the conversion module comprises:
a. a conversion algorithm used for calculating the condition value, wherein the condition value has a mathematical relationship to the adapter output data;
b. computer instructions instructing the computer processor to receive a field of vision data, wherein the field of vision data comprises at least one of:
  (i) the adapter output data;
  (ii) data stored in the adapter nonvolatile data storage;
  (iii) manually inputted data; and
  (iv) historical data for the optical device;
c. computer instructions instructing the computer processor to time synchronize the adapter output data if necessary;
d. computer instructions instructing the computer processor to allow a user to select a target for which the condition value is calculated, wherein the target is selected from the field of vision data;
e. computer instructions instructing the computer processor to compare the field of vision data with the conversion algorithm to calculate the condition value;
f. computer instructions instructing the computer processor to adjust the condition value based upon the calibration data; and
g. computer instructions instructing the computer processor to output the condition value.

* * * * *